United States Patent [19]

Eibl

[11] 4,062,754

[45] Dec. 13, 1977

[54] APPARATUS FOR DESTROYING MICROORGANISMS IN AN AQUEOUS LIQUID BY ELECTROLYTIC OXIDATION

[75] Inventor: Volker Eibl, Munich, Germany

[73] Assignee: Sachs Systemtechnik GmbH, Schweinfurt am Main, Germany

[21] Appl. No.: 608,245

[22] Filed: Aug. 27, 1975

[30] Foreign Application Priority Data

Sept. 5, 1974 Germany .............................. 2442474

[51] Int. Cl.² .............................................. C02B 1/82
[52] U.S. Cl. ..................................... 204/268; 204/269
[58] Field of Search ............... 204/149, 152, 255, 275, 204/272, 268, 269

[56] References Cited

U.S. PATENT DOCUMENTS

| | | | |
|---|---|---|---|
| 820,113 | 5/1906 | Hinkson | 204/268 |
| 883,170 | 3/1908 | Christy | 204/268 |
| 1,440,091 | 12/1922 | Long | 204/272 |
| 1,547,362 | 7/1925 | Casale | 204/272 X |
| 1,925,322 | 9/1933 | Hills | 204/269 X |
| 3,402,117 | 9/1968 | Evans | 204/268 |
| 3,779,889 | 12/1973 | Loftfield | 204/268 |
| 3,835,020 | 9/1974 | Galneder | 204/268 |

FOREIGN PATENT DOCUMENTS

| | | |
|---|---|---|
| 430,477 | 6/1935 | United Kingdom. |
| 433,576 | 8/1935 | United Kingdom. |

Primary Examiner—Arthur C. Prescott
Attorney, Agent, or Firm—Hans Berman

[57] ABSTRACT

The disinfecting effect of electric current passing between a contaminated aqueous liquid and an anode immersed in the liquid is enhanced by providing bipolar electrodes between the directly energized anode and cathode so that the flow channels for the liquid between the electrode faces are limited to a width of 3 mm or less, the auxiliary electrodes being insulated from each other and from the directly energized electrodes and disposed in such a manner that the potential difference between each pair of adjacent electrodes is equal.

10 Claims, 3 Drawing Figures

APPARATUS FOR DESTROYING MICROORGANISMS IN AN AQUEOUS LIQUID BY ELECTROLYTIC OXIDATION

This invention relates to the destruction of microorganisms in aqueous liquids, and particularly to apparatus for destroying microorganisms in an aqueous liquid by electrolytic oxidation.

It is known to pass a contaminated aqueous liquid through an electrolytic cell while a voltage is applied to electrodes in the cell, and to destroy microorganisms in the liquid by exposure to the anolyte.

It has been proposed in the German Pat. application No. 2,337,355, published without examination, to purify water of heavy metal ions, cyanides, sludge, coloring matter, organic ions and compounds in an electrolytic cell packed with spherical auxiliary electrodes which are insulated from each other and from the directly energized electrodes. It has now been found that the spherical auxiliary electrodes, because of their tight packing, shield each other so that the potential distribution among the auxiliary electrodes is uneven, and the oxidizing effect on the contaminants is limited. This is tolerable when contaminants of the afore-described types are to be reduced to an acceptable level, but not sufficient if the contaminants are viable microorganisms which multiply again unless practically completely destroyed by the treatment. The known process thus is not practical in the removal of microorganisms from drinking water.

It is the primary object of this invention to provide electrolytic apparatus which permits effective destruction of microorganisms in drinking water and like aqueous liquids.

A complementary object is the provision of such apparatus which is of small bulk even when suitable for treating aqueous liquids at a high rate.

It has been found that these objects can be achieved in an apparatus in which a row of electrodes is mounted in a cavity of a vessel in spaced, electrically insulated relationship. The row includes two terminal main electrodes and a plurality of auxiliary electrodes interposed between the main electrodes. Each main electrode has a face spacedly opposite the corresponding face of the other main electrode, and each auxiliary electrode has two faces substantially parallel to the faces of the two main electrodes. The faces of each pair of adjacent electrodes in the row define therebetween a channel for flow of liquid parallel to the defining faces.

The main electrodes may be connected conductively to respective terminals of a source of electric power for thereby establishing a voltage between the main electrodes. An inlet and an outlet are provided on the vessel for passing therebetween respective portions of a stream of liquid through the channels. Each of the stream portions provides the sole path of electric current between the pair of electrodes defining the associated channel. The spacing of the electrodes in each pair is such that the potential differences between the electrodes of each pair of adjacent electrodes in the row are equal when a voltage is established between the main electrodes and the stream of aqueous liquid is passed through the several channels.

Other features, additional objects, and many of the attendant advantages of this invention will readily be appreciated as the same becomes better understood from the following detailed description of preferred embodiments when considered in connection with the appended drawing in which.

Figure 1:
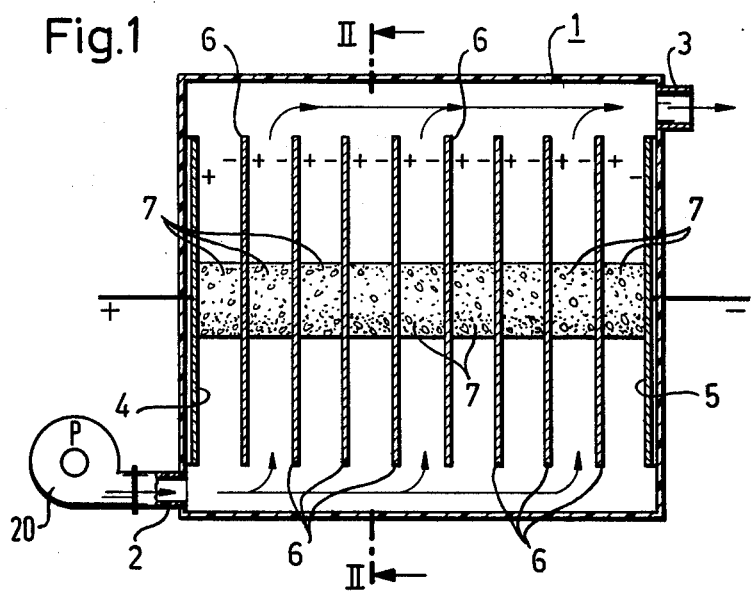
FIG. 1 shows electrolytic apparatus of the invention in elevational section.

Referring now to the drawing in detail, and initially to FIG. 1, there is shown a cylindrical vessel 1 of insulating plastic. An inlet nipple 2 is mounted on the lowermost portion of one circular end wall of the vessel 1, and an outlet nipple 3 is provided at the highest point of the other circular vessel wall. Electrodes 4, 5, of stainless steel sheet stock (Type AISI 316) are adhesively fastened to the inner faces of the two end walls, and eight auxiliary electrodes 6 of the same material are evenly spaced between the electrodes 4, 5 by somewhat resilient, cylindrical spacers 7 of polyurethane foam, the spacers being loaded in compression to clamp the electrodes 6 in the illustrated position in which their major faces are parallel to each other and to the exposed faces of the main electrodes 4, 5. The latter are connected by respective leads to the positive and negative terminals of a rectifier indicated by + and − signs.

Figure 2:
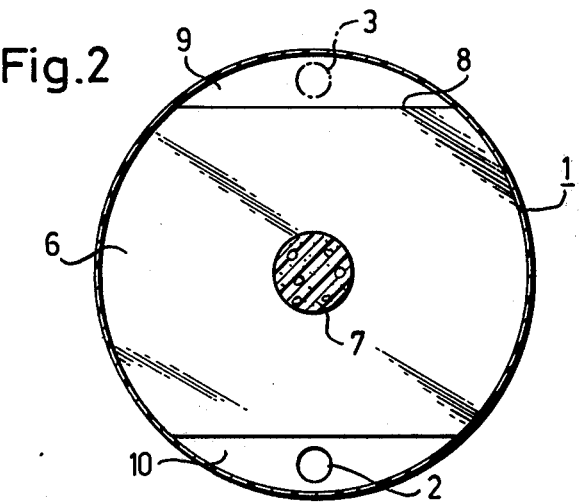
FIG. 2 illustrates the apparatus of FIG. 1 in section on the line II — II in FIG. 1.

As seen in FIG. 2, the several, plate-shaped electrodes 4, 5, 6 have identical configurations of a segment of a circle bounded by two parallel chords 8 equidistant from the center of the circle. The chords are aligned in the direction of the vessel axis to define a collecting duct 9 communicating with the outlet 3 and a distributing duct 10 communicating with the inlet 2. The arcuate edges of the electrodes are sealed to the cylindrical vessel wall. A pump 20 feeds the liquid to be purified to the inlet 2 at a constant rate, and the stream of liquid is distributed by the duct 10 among the several transverse channels between respective faces of adjacent electrodes 4, 5, 6. The portions of the stream emerge from the channels into the collecting duct 9, and the liquid is discharged from the outlet 3. The spacers 7 are of so much smaller diameter than the electrodes as not significantly to affect the liquid flow through the channels.

When the rectifier applies a voltage between the anode 4 and the cathode 5, the auxiliary electrodes 6 become bi-polar, their faces directed toward the anode 4 becoming cathodic, and the faces directed toward the cathode 5 becoming anodic. Because of the uniform spacing of the identical electrodes 4, 5, 6 which bound each of the several channels between the ducts 9, 10, the potential differences between the electrodes of each pair bounding a channel are equal.

The number of auxiliary electrodes 6 in the illustrated apparatus may be varied to suit specific condition, but is preferably not smaller than three. The following Examples illustrate the operation of apparatus of the general type shown in FIGS. 1 and 2.

EXAMPLE 1

The electrolytic cell employed had two main electrodes and 55 auxiliary electrodes, and each electrode face had an area of 95 cm$^2$. The total anodic surface area engaged by the flowing liquid thus was 5,320 cm$^2$. The channels between adjacent electrode faces had a uniform width of 2 mm. The vessel 1 had an outer diameter of 133 mm.

The cell was used for disinfecting drinking water contaminated with 2.8 × 10$^6$ cells of E. coli per milliliter and having a specific resistivity of 2,200 ohms.cm.

The voltage across the main electrodes was set to produce an anode current density of 5 mA/cm². The contaminated liquid was pumped through the cell at such a rate that the average dwell time in the channels between the electrodes was 31 seconds. No viable microorganisms could be detected in the purified water discharged from the outlet 3.

EXAMPLE 2

In an apparatus having only seven auxiliary electrodes and a correspondingly shorter vessel, but not otherwise significantly different from that employed in Example 1, drinking water contaminated with $1.9 \times 10^5$ E. coli per ml was treated between the electrodes having a combined anode area of 760 cm² for an average dwell time of 15 seconds at an anode current density of 1.5 mA/cm², the electrode faces being spaced 2.0 mm apart. No viable germs could be detected in the treated water.

For best current efficiency, the anode current density should not exceed 8 mA/cm², and other parameters should be selected to maintain a potential difference of at least 1.5 volt between electrodes bounding a flow channel therebetween.

The disinfecting effect of the oxidizing compounds formed at the anodes is not materially affected by the hydrogen simultaneously generated at the cathodic electrode surfaces. Any undesirable effects that nascent hydrogen may have are readily avoided by covering the cathodic electrode faces with a porous non-conductive material which impedes migration toward the cathode face.

While continuous direct current was supplied to the electrodes in the Examples described above, pulsed or intermittent direct current, as furnished by a half-wave rectifier, is equally effective. The cells of the type shown in FIGS. 1 and 2 are of simple design, make effective use of the current supplied, and may be modified readily for adaptation to available sources of electric power. When the electrodes are replaced by others of equal number, but greater area, the resistance of the cell is decreased, and an effective current can be produced by a smaller applied voltage. Increasing the number of electrodes at unchanged individual surface area increases the electrical resistance of the cell and thus adapts the cell to a power source of higher voltage under otherwise identical conditions.

Other parameters being comparable, the largest possible number of auxiliary electrodes is desirable. The multiplicity of flow channels permits treatment of the aqueous liquid at a high rate, yet the narrowness of individual channels, preferably 3 mm or less, causes each contaminating microorganism to move past an anode at a distance small enough for interaction with the somewhat labile anodic products of electrolysis other than molecular oxygen.

To operate at the elevated voltage necessitated by a large number of auxiliary electrodes is generally advantageous because of the lower energy losses in bus bars and other conductors. To use fewer than three auxiliary electrodes has been found to reduce the germicidal effect of the treatment.

The capacity of apparatus of the invention for successfully treating contaminated aqueous liquids, of which drinking water is merely a characteristic example, has been found to be related to the total available anode area which in turn is one half of the combined surface area of the main and auxiliary electrodes engaged by the liquid flowing through the apparatus. The following, empirically developed relationship has been found to hold:

$$F = K \times v$$

In this equation, F is the numerical value (in cm²) of the combined area of the anodic electrode surfaces in the cell, $v$ is the numerical value (in cm³/sec.) of the rate of liquid flow through all channels between the electrodes, and K is a factor whose numerical value is between 30 and 160 and which remains unchanged for a chosen applied cell voltage, thus permitting adjustment of anode area for different flow rates controlled, for example, by varying the rotary speed of the pump 20 without loss of cell effectiveness, or vice versa.

The apparatus shown in FIGS. 1 and 2 combines desirable hydrodynamic and electrical properties, but is capable of many modifications without significant change in function or loss of effectiveness. One such modification is shown by way of example in FIG. 3.

The modified apparatus has a cathode 11 which is a cylindrical rod of austenitic stainless steel, a tubular anode 12, and three auxiliary electrodes 13 which are cylindrical, stainless steel tubes of varying diameter coaxial with each other and with the main electrodes 11, 12. The five electrodes radially define four, coaxial, annular flow channels which connect two insulating headers 14, 15. The headers, jointly with the tubular anode 12, constitute the outer walls of the cell casing or vessel, and the cathode rod 11 and auxiliary electrodes 13 are secured to the headers by insulating fasteners 16. The liquid to be purified is admitted to the header 14 by an inlet 17 from a non-illustrated pump, and the treated liquid is discharged from the header 15 through an outlet 18.

Figure 3:
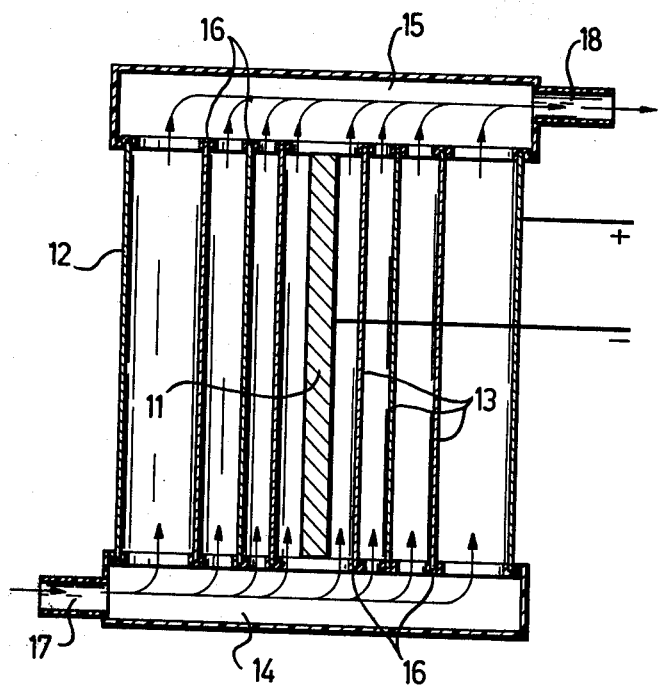
FIG. 3 shows another apparatus of the invention in elevational section.

Because the electrode faces are arcuate about a common axis at different radii of curvature, their surface areas differ, and the required equal potential difference between radially adjacent electrodes is maintained by varying the radial width of the flow channels between adjacent electrodes, the channel partly bounded by the anode 12 being widest, and that adjacent the cathode rod 11 being narrowest, as is generally indicated in FIG. 3 which, however, is not drawn to scale.

The apparatus described above with reference to FIG. 3 is functionally closely analogous to the embodiment of the invention illustrated in FIGS. 1 and 2. It operates in the same manner not requiring separate description, and is affected by the same operating variables in substantially the same manner.

It should be understood, of course, that the foregoing disclosure relates only to preferred embodiments of the invention, and that it is intended to cover all changes and modifications of the examples of the invention herein chosen for the purpose of the disclosure which do not constitute departures from the spirit and scope of the invention set forth in the appended claims.

What is claimed is:

1. Apparatus for destroying microorganisms in an aqueous liquid comprising:
    a. a vessel bounding a cavity;
    b. a row of electrodes mounted in said cavity in spaced, electrically insulated relationship and including two terminal, main electrodes and at least one auxiliary electrode interposed between said main electrodes, 1. each main electrode having a face spacedly opposite the corresponding face of the other main electrode,
2. said at least one auxiliary electrode having two faces substantially parallel to said respective faces of said main electrodes, said two faces being arcuate about a common axis of curvature, the axes of curvature of the faces of said at least one auxiliary electrode substantially coinciding,
3. respective faces of each pair of adjacent electrodes in said row defining therebetween a channel for flow of liquid parallel to the defining faces;

c. conductive means for connecting said main electrodes to respective terminals of a source of electric power and for thereby establishing a voltage between said main electrodes;

d. inlet means and outlet means on said vessel for simultaneously passing therebetween respective portions of a stream of aqueous liquid through said channels, each of said portions providing the sole path of electric current between the pair of electrodes defining the associated channel.

2. Apparatus as set forth in claim 1, wherein said row includes a plurality of said auxiliary electrodes, said auxiliary electrodes being tubular and coaxial.

3. Apparatus for destroying miroorganisms in an aqueous liquid comprising:
  a. a vessel bounding a cavity;
  b. a row of electrodes mounted in said cavity in spaced, electrically insulated relationship and including two terminal, main electrodes and at least one auxiliary electrode interposed between said main electrodes,
    1. each main electrode having a face spacedly opposite the corresponding face of the other main electrode,
    2. said at least one auxiliary electrode having two faces substantially parallel to said respective faces of said main electrodes,
    3. respective faces of each pair of adjacent electrodes in said row defining therebetween a channel for flow of liquid parallel to the defining faces, the width of each of said channels between the faces defining the same being no greater than 3 millimeters;
  c. conductive means for connecting said main electrodes to respective terminals of a source of electric power and for thereby establishing a voltage between said main electrodes;
  d. inlet means and outlet means on said vessel for simultaneously passing therebetween respective portions of a stream of aqueous liquid through said channels, each of said portions providing the sole path of electric current between the pair of electrodes defining the associated channel.

4. Apparatus as set forth in claim 3, wherein said row includes at least three of said auxiliary electrodes.

5. Apparatus as set forth in claim 3, further comprising means defining a distributing duct and a collecting duct, said distributing duct communicating with said inlet means and with a first portion of each of said channels, and said collecting duct communicating with said outlet means and a second portion of each of said channels, the first and second portions of each channel being spaced in the direction of said flow of liquid.

6. Apparatus as set forth in claim 5, wherein said direction is vertical.

7. Apparatus as set forth in claim 3, further comprising spacers between the faces of each pair of adjacent electrodes, the spacers having a constant cross section along the entire distance between the faces and the peripheral surface of the spacers extending perpendicularly to the electrode faces.

8. Apparatus as set forth in claim 7, wherein the spacers are cylindrical and the axes of the cylindrical spacers extend perpendicularly to the electrode faces.

9. Apparatus as set forth in claim 3, further comprising a spacer in each of said channels interposed between the faces of the pairs of electrodes defining said channels respectively, the cross section of each spacer parallel to said faces being uniform and smaller than the area of said faces over the entire distance of said faces, the faces of each of said pairs projecting in all directions beyond the interposed spacer.

10. Apparatus as set forth in claim 3, wherein said at least one auxiliary electrode is plate-shaped, and said two faces of said at least one electrode are substantially planar.

* * * * *